Figure 1:
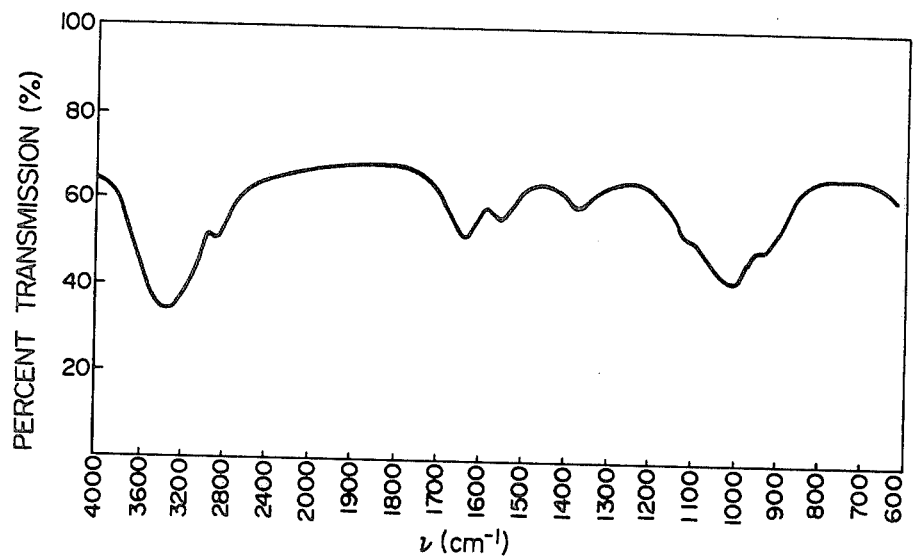

United States Patent [19]

Ogino et al.

[11] 4,209,507

[45] Jun. 24, 1980

[54] NOVEL ANTI-TUMOR SUBSTANCE AND PREPARATION THEREOF

[75] Inventors: Shigeo Ogino, Nishinomiya; Noboru Yoshida, Saitama; Takao Kiyohara, Ibaraki, all of Japan

[73] Assignee: Sumitomo Chemical Company, Ltd., Osaka, Japan

[21] Appl. No.: 922,196

[22] Filed: Jul. 5, 1978

[30] Foreign Application Priority Data

Jul. 11, 1977 [JP] Japan .................................. 52-83129

[51] Int. Cl.$^2$ .......................... A61K 35/74; C12P 1/04
[52] U.S. Cl. .................................... 424/116; 435/170; 435/822

[58] Field of Search ................ 195/96, 80 R; 424/116; 435/170

[56] References Cited

PUBLICATIONS

Lennette et al., Manual of Clinical Microbiology, 2nd ed., pp. 274–276 (1974).

*Primary Examiner*—Alvin E. Tanenholtz
*Attorney, Agent, or Firm*—Cushman, Darby & Cushman

[57] ABSTRACT

Antitumor substances are prepared by culturing a microorganism, *Acinetobacter calcoaceticus*. The antitumor substances have potent antitumor activity as well as immunostimulatory activity and are effective in a very small amount without harmful effects such as toxicity.

8 Claims, 2 Drawing Figures

NOVEL ANTI-TUMOR SUBSTANCE AND PREPARATION THEREOF

The present invention relates to antitumor substance having excellent antitumor activity as well as potent immunostimulatory activity, and to a process for producing the same, which comprises culturing a microorganism belonging to the genus Acinetobacter in a suitable culture medium and thereafter isolating antitumor substance therefrom.

It is well known that a variety of materials have been used in the past for the treatment of tumors and many of them are cytotoxic and liable to cause harmful effects on hosts. It is reported, for example, that many patients who have received cytotoxic antitumor agents are immunosuppressed, which might cause secondary infectious diseases or relapses of the disease, and therefore stimulation of immune function is necessary. Accordingly, the so-called immunotherapy has been developed in recent years, wherein many materials, both biological or chemical, are administered to tumor-bearing patients to stimulate the immune responses, thereby effecting tumor-inhibitory effects.

In view of the recent development of immunostimulatory therapy, we have carried out an extensive study seeking microorganisms capable to produce antitumor substance having immunostimulating activity as well as direct tumor-inhibitory activity. As the result, it has now been found that a microorganism belonging to the genus Acinetobacter produce and extracellulary accumulate antitumor substance having excellent antitumor activity and potent immunostimulating activity when cultured in a relatively simple culture medium. More specifically, the antitumor substance obtained from culture broth of said microorganisms not only inhibits growth of experimental tumors but also extinguishes solid tumors. Further, the antitumor substance of the present invention also proved to possess potent immunostimulating activity and low toxicity. Thus, the antitumor substance of the present invention has been found to be useful as antitumor agents and immunostimulants.

Accordingly, the present invention provides substance useful for the treatment of tumors and a pharmaceutical composition containing said antitumor substance as an active ingredient, and it also provides a process for producing antitumor substance by culturing said microorganism in a suitable medium and isolating it therefrom.

In the present invention, antitumor substance can be prepared by culturing *Acinetobacter calcoaceticus*, particularly its new variant, *Acinetobacter calcoaceticus* var. microformis SC-1714, in a suitable medium and thereafter isolating it from the culture broth.

In the following, the characteristics of said newly found microorganism, *Acinetobacter calcoaceticus* var. microformis SC-1714 are described:

1. Morphology

Cells spherical, sometimes short rod-shaped, occurring singly, in pairs or aggregates. Dimensions, 0.6 to 1.1 microns in diameter. Non-motile. No spores formed. Gram-negative. Acid-fast stain negative.

2. Growth on various culture media
   (1) Agar-bouillon plate (cultivated at 28° C. for 48 hours)
   Abundant growth with rising. Mucoid colonies with peripheral completely circular to wavy, white to pale reddish yellow in color, with dull lustre and intransparent.
   (2) Agar-bouillon slant (cultivated at 28° C. for 48 hours)
   Abundant growth with rising. Colonies smooth and mucoid, white to pale reddish yellow in color, with dull lustre and intransparent.
   (3) Liquid bouillon (cultivated at 28° C. for 24 hours)
   Moderately turbid, with formation of fragile pellicles and viscous sediments.
   (4) Bouillon-gelatin stab (cultivated at 28° C. for 30 days)
   Growth on surface. Colonies mucoid and not liquefied.
   (5) Litmus milk (cultivated at 28° C. for 4 days)
   Acidified with coagulation.
   (6) Media King A and King B (cultivated at 28° C. for 7 days)
   Pale yellow diffusible pigments formed in both media.

3. Physiological properties:
   (1) Growth temperature: 20° to 45° C., optimum temperature being 30° to 37° C.
   (2) pH range: 5.0 to 8.5, optimum pH range being about 7.0
   (3) Nitrates: not reduced
   (4) Denitrification reaction: negative
   (5) MR test: negative
   (6) VP test: negative
   (7) Indole formation: none
   (8) Sulfide formation: none
   (9) Starch hydrolyzed
   (10) Citric acid utilized
   (11) Utilization of nitrogen sources: Growth possible by utilizing ammonium salts
   (12) Urease: absent
   (13) Catalase: present
   (14) Oxidase: absent
   (15) Aerobic
   (16) O-F test: oxidative
   (17) Acid and gas formation from carbohydrates:
   Acid is formed but no gas formed from xylose, glucose, mannose, galactose, lactose, and dextrin; neither acid nor gas is formed from arabinose, fructose, maltose, saccharose, trehalose, raffinose, sorbitol, innositol, mannitol, glycerine, starch, inulin, salicin, α-methyl glucoside.
   (18) Cellulose decomposed
   (19) Lysine decarboxylase activity: weakly positive
   (20) Haemolysis: positive
   (21) Susceptibility to antibiotics: resistant to 20 units of penicillin G
   (22) Nutrient demands: No special demand, with sufficient growth in a simple medium such as peptone water The above characteristics are substantially the same as those of genus Acinetobacter, (The genus Acinetobacter has only one species, namely *Acinetobacter calcoaceticus*) belonging to the family of Neisseriaceae, as described in Bergey's Manual of Determinative Bacteriology, eighth edition, 1974. But, when compared in further detail, *Acinetobacter calcoaceticus* is shaped primarily in short rods, sometimes in spheres, with dimensions of 1.0 to 1.5 by 1.5 to 2.5 microns, as different in shape and dimensions from the present strain. Accordingly, the present strain is identified to be a variant of *Acinetobacter calcoaceticus* and named as *Acinetobacter calcoaceticus* var. microformis SC-1714 and deposited at American Type Culture Collection, U.S.A., under the deposition No. ATCC-31299 and also at Fermentation Research Institute, Agency of Industrial Science and Technology, Japan, under the deposition No. FERM-P-4064.

In the present invention, the antitumor substance can be obtained in various forms from the culture broth of said microorganism. For instance, it can be obtained as a culture fluid by simply removing the microbial cells from the culture broth, or it may be isolated from the culture broth as precipitates by applying methods conventionally used for the isolation of high molecular natural substance, which may be further purified by a conventional method to give high molecular substance (hereinafter "high molecular substance SC-1714").

In order to obtain said antitumor substance, said microorganism is inoculated onto a suitable agar medium and cultivated at a suitable temperature, preferably in the range from 25° to 37° C., most preferably at 30° C., for several days, preferably from 2 to 3 days. This seed culture, after being confirmed of absence of contamination, is then inoculated in a liquid or a solid medium to carry out cultivation at a suitable temperature.

In the present invention, cultivation in a liquid medium refers to a cultivation under a stationary way, shaking, aeration or aeration and stirring. The solid medium includes agar, gelatin, starch, etc. or a suitable combination thereof. As a cultivation for producing the active substances as described above, either liquid or solid medium can be used. But a liquid medium is more convenient from standpoint of handling and productivity. Conventional media can sufficiently be used as a medium for cultivation of the microorganism producing the above active substances, so far as nutrient ingredients necessary for growth of the above organism and production of said antitumor substances are contained in the medium. Namely, glucose, maltose, lactose or sugar molasses can be used as carbon source; peptone, meat extract, malt extract, corn steep liquor, yeast extract, distillers, soybean proteolysis products, or amino acids as nitrogen source. If desired, inorganic nitrogen source such as ammonium salts can also be used. Other inorganic salts, including phosphoric acid salts, magnesium salts, sodium salts, iron salts, or various vitamins can also optionally be added.

The initial pH for cultivation is adjusted at about neutral values, preferably at 6.0 to 7.5. The cultivation temperature is variable within the range at which said microorganism can grow and produce said antitumor substances, but it preferably falls within the range from 25° to 35° C. The cultivation time differs depending on the cultural conditions, but usually from one to two days. Cultivation may be terminated optimally at the time when the amount of said antitumor substances accumulated in the medium appears to be at its maximum. As mentioned above, either stationary, shaking, aerating or aeration-stirring cultivation may be available. Among them, shaking or aeration-stirring cultivation is preferred. Shaking culture may suitably be carried out at a stroke of 5 to 20 cm at the rate of 30 to 200 r.p.m.; while aeration-stirring cultivation under aeration of 0.1 to 2.0 liter/liter-medium/min. at a stirring speed of 30 to 800 r.p.m.

The culture broth after completion of cultivation, which contains a considerable amount of antitumor active substance, can be provided for use as antitumor substances as it is or as lyophilized powders after removal of cells in case of a liquid cultivation. Removal of microbial cells can be conducted, after optionally adjusting pH of the culture broth, by way of centrifugation or filtration using filtrating aids such as hyflo-super cells. Centrifugation method is better in efficiency of separation. For the purpose of avoiding re-growth of said microorganism which may possibly be remained in the culture broth after removal of microbial cells by means of centrifugation, etc., the filtrate is further subjected to removal of cells using a bacteria filter, such as Millipore filter HAWPO 2500 (0.45 micron or less; trade name, Millipore Co., U.S.A.) or Seitz bacteria filter. Furthermore, if necessary, an antibiotic substance such as streptomycin may be added at a final concentration of, for example, 100 mcg/ml or more for prevention of growth of said microorganism or other bacteria floating in the air which may possibly be contaminated during operational procedures. The thus treated filtrate, with or without addition of said antibiotic substance, can be stored by being filled in a sterilized ampoule, followed by sealing under aseptic conditions. If storage under a solution state is not desirable, it may be converted to lyophilized powders.

Alternatively, the antitumor substances can be provided as precipitates which may be formed by such methods as by adding an acidic substance to the culture broth after removal of cells to lower pH less than 2 thereby to form amorphous precipitates; by adding a salt such as ammonium sulfate to a 70% or higher saturation concentration under cooling; or by adding a hydrophilic organic solvent such as acetone, methanol, ethanol, etc. under cooling to a concentration of 60% or higher (organic solvent precipitation method); and so on. The precipitation method by addition of an acidic substance is liable to inactivate biological activity, while recovery of active substances is lower in case of the precipitation method by addition of a salt. Therefore, for higher recovery of active substances without damaging activities thereof, it is preferred to adopt a precipitation method by adding an organic solvent such as acetone or ethanol to a concentration of 60% or more. Referring now in further detail to the most efficient organic solvent precipitation method, with or without addition of a precipitation-accelerator such as calcium chloride powders in an amount of 0.1 to 1% (W/V), preferably 0.8%, to the culture broth after removal of cells, a water-soluble solvent such as acetone, methanol, ethanol etc. or a combination of two or more of said solvent is added in a great excess, at least at a concentration of 60% or more, under cooling, preferably at around 5° C. The mixture is left to stand overnight at a low temperature, for example, at 5° C. until complete formation of precipitates. The resulting precipitates are collected by decantation or filtration and dissolved in water. If desired, re-precipitation may be carried out by addition of the above solvent to the resulting solution to a concentration of 60% or more, whereby amorphous precipitates having antitumor activity can be obtained. In the present invention, for the purpose of purification, the precipitates containing active substances obtained by the above method are usually collected, dissolved in water and then deionized and decolored with ion-exchange resins such as Dowex 1×2, Dowex 50, Duolite S-30, and the like. Prior to said deionization and decoloration, salting out may be carried out by saturating the solution with an inorganic salt such as ammonium sulfate. Purification treatments can be carried out according to various orders, for example, in the order of salting out, dialysis and deionization or salting out, deionization and dialysis, etc. A part of these treatments can also be used in combination, if desired.

The precipitates formed by addition of a water-miscible organic solvent such as acetone, methanol, ethanol, etc. in a great excess, at least 60%, to the aqueous solution of the active substances obtained by the above procedure are washed thoroughly with 90% or more of the aforesaid organic solvent, if necessary, before they are dried by using acetone or ether or dissolved again in water, followed by lyophilization to give crude powders of the active substances. The thus obtained crude powders may optionally be dissolved in water to prepare an aqueous solution. The resulting solution is subjected to defatting procedure with a mixture of chloroform-methanol according to the method of Folch et al. (J. Folch et al: The Journal of Biological Chemistry, Vol. 226, p. 497, 1957) to remove substances irrelevant with said activity, whereby water-solubility of the substances is preferably increased.

The objective active substances from the above crude powders can be isolated by the following procedures. The crude powders are dissolved in a small amount of water and subjected to ion-exchange and molecular sieve chromatography with carboxymethyl-Sephadex (CM-Sephadex). The non-adsorbed fractions eluted by washing with water are further adsorbed on anion-exchanger such as diethylaminoethyl cellulose (DEAE-cellulose). After washing well with water, the salt concentration of eluate is increased by preferably eluting with a saline water with a concentration of 0.5 to 1.0 mol/liter. The fractions in which activity is detected are collected and desalted by molecular sieve chromatography using, for example, Sephadex G-100 or by dialysis with cellophane tubes, followed by lyophilization, to give the objective substances as white powders. Alternatively, without use of ion-exchanger, the above crude powders are dissolved in a small amount of water and subjected to molecular sieve chromatography using, for example, a Sepharose 4B. The eluted active fractions are collected, optionally, dialyzed and lyophilized to give the objective substances as white powders.

The substances obtained by the method of the present invention are non-hygroscopic powders showing no distinct melting point and an aqueous solution thereof is substantially neutral or weakly acidic. The present substances are found to contain 15 to 17% of protein calculated as bovine serum alubumin by quantitative analysis of protein by Copper-Folin method and 50 to 51% of saccharide calculated as glucose by quantitative analysis of neutral saccharide by phenol-sulfuric acid method. These values are not always constant because the compositions of the product obtained will vary depending on the culture conditions and the method of purification.

The substance SC-1714 obtained according to the procedure as described above of the present invention is weakly positive to ninhydrin reaction. Its antitumor activity is weakened when decomposed with a proteolytic enzyme such as pronase, papain, etc. When this substance is partially decomposed with a carbohydrase such as glucosidase, its antitumor activity is also weakened. On the other hand, when this substance is decomposed at a high temperature in a strongly acidic or alkaline solution, its biological activities such as antitumor activity are completely vanished. The molecular weight is assumed to be greater than, at least 5000.

The high molecular substance SC-1714 obtained according to the procedure as described above of the present invention has the physical, chemical and biological properties as shown below:

Physical and chemical properties

Figure 2:
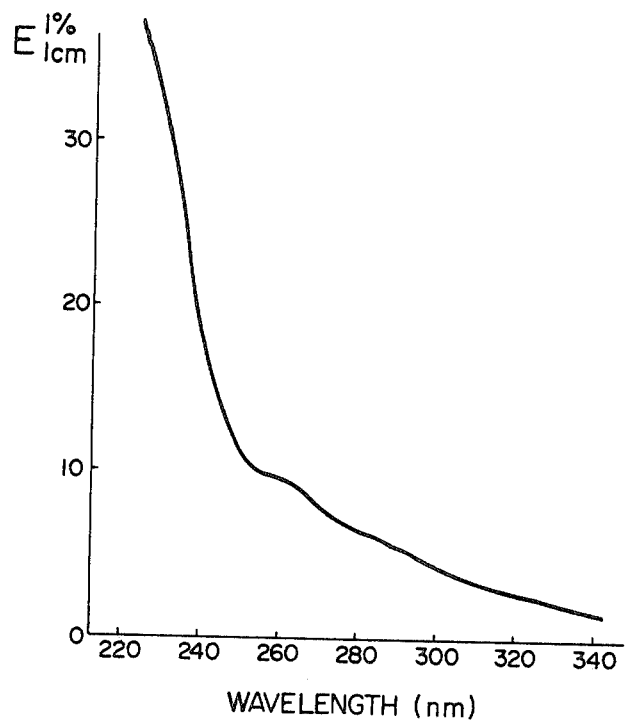

1. Appearance and solubility: obtained as white powders or films, soluble in water but insoluble in organic solvents
2. Decomposition point: higher than 235° C.
3. Ultra-violet absorption spectrum: as shown in FIG. 1 (for the product of Example 5), with strong absorption at terminal end and weak absorption at around 260 nm
4. Infrared absorption spectrum (KBr tablet): as shown in FIG. 2 (for the product of Example 5), with specific absorptions at 3600, 1650, 1550 and 1100–1000 $cm^{-1}$
5. Elemental analysis: C 33.7–38.9%; H 5.2–6.9%; N 2.3–3.0%
6. Color reactions: slightly positive to positive to ninhydrin reaction, xanthoprotein reaction and biuret reaction; positive to Molisch reaction, anthrone-sulfuric acid reaction, phenolsulfuric acid reaction and carbazole-sulfuric acid reaction
7. Color reaction of hydrolyzed products: ninhydrin reaction intensified (after hydrolysis in 1 N HCl, at 105° C. for 24 hours); negative to phloroglucin reaction (after hydrolysis in 1 N $H_2SO_4$ at 100° C. for 4 hours)
8. Stability: Stable at pH 5 to 8 at 0° to 60° C.

Biological properties

1. Biological activity: having no antimicrobial activity, having antitumor activity, immunostimulating activity, anti-vaccinia virus activity, antiinflammatory activity and activity for inhibiting secretion of acid in the stomach
2. Acute toxicity: acute toxicity for mouse (ICR type, male, 20 to 25 g) by one dosage is as follows;
   $LD_0$ 1 g or more/kg (oral administration)
   $LD_{100}$ 300 mg/kg (intraperitoneal and intravenous injection)

Antitumor tests are carried out use of SC-1714 in the following manner:

(1) The test tumors used are ascites form of Sarcoma 180 and Ehrlich carcinoma of mouse. The first administration of medicine is given after three hours after transplantation of cancer cell and subsequent administrations once every day, for 6 days, by interaperitoneal injection at a dose of 5 mg/kg. The results of the effect of life prolongation as compared with Control group are shown in Table 1.

Table 1

| Life prolongation effect for mouse ascites cancer | | |
|---|---|---|
| Carcinoma | Dosage | Percentage of life prolongation (T/C %)* |
| Sarcoma 180 | 5 mg/kg × 6 times | more than 200% |
| Ehrlich carcinoma | " | more than 200% |

*T/C % = (Average of survival days for treated group of mice/average of survival days for Control group of mice) × 100

(2) The effect of the medicine on the growth of solid of forms of Sacroma 180 and Ehrlich carcinoma of mouse is observed. Administrations of the medicine are given after 24 hours after transplantation of tumors by way of intraperitoneal injection, intravenous injection, subcutaneous injection or oral administration at a dose of 0.5 to 2 mg/kg once every other day for 5 times. On the next day after the final administration, solid tumors are taken out and compared with those of control group to be expressed in terms of tumor-inhibiting percentage, as shown in Table 2. From autopsy, it is observed that growth of most of the solid tumors in the treated group is inhibited and there is only found a mass of connective tissue. On the next day after the first administration, temporary reduction of body weight of mouse is observed, but the treated group show substantially the same extent of weight gain as the control group over the test period.

Table 2

Inhibitory percentage for solid tumors of mouse

| Dosage | Method of administration | Inhibitory percentage for Sarcoma 180 (solid) | Inhibitory percentage for Ehrlich carcinoma (solid) |
|---|---|---|---|
| 2 mg/kg × 5 | Intraperitoneal injection | 100% | 100% |
| 1 mg/kg × 5 | Intraperitoneal injection | 95% | 92.2% |
| 0.5 mg/kg × 5 | Intraperitoneal injection | 72% | 75% |
| 2 mg/kg × 5 | Intravenous injection | 100% | |
| 2 mg/kg × 5 | Subcutaneous injection | 95% | |
| 2 mg/kg × 5 | Oral administration | 88% | |
| 0.5 mg/kg × 5 | Oral administration | 67% | |

(3) To ICR-type mouse (male, 5 weeks old, body weight: 20 to 22 g) are transplanted subcutaneously $10^6$ of Sarcoma 180 cancer cells. One week after transplantation, only mice, in which the cancer cells are observed to be surely transplanted and grow as tumors or solid cancer, are selected and observation is continued for both administered group and Control group, each group consisting of 10 mice. The first administration is given one week after transplantation and thereafter every other day for 10 times, whereby solid cancers are observed daily. Five days after the 10th administration, measurement of average body weight gain and autopsy are carried out to see whether there is any harmful effect. From periodical observation of the antitumor activity of the high molecular weight compound of the present invention, the growth of tumors begins to be terminated or regressed until tumors are found to be completely vanished in many of the mice two weeks after administration of the medicine. The result is shown in Table 3.

Table 3

Anti-tumor effect against mouse-Sarcoma 180 solid cancer

| Dosage | Ratio of mice in which complete regression was observed | Percentage of inhibition |
|---|---|---|
| 2 mg/kg × 5 | 6/10 | 90.7% |

(4) To mouse (ICR-type, male, 20 to 22 g) is administered the substance obtained by the present invention at a dose of 2 mg/kg every day for five days for pre-treatment. Then, $10^6$ of Sarcoma 180 cancer cells are subcutaneously transplanted and observation is continued daily. Formation of solid cancer is found to be potently inhibited. Namely, one week after transplantation, even the effectively transplanted cells proliferate only to less than 20% in size of the cancer mass as compared with that of Control group. In most of the mice, no cancer mass is recognized to show failure of transplantation.

(5) To mouse (ICR-type, male, 20 to 22 g) is administered the substance obtained by the present invention at a dose of 2 mg/kg every other day for five times by intraperitoneal injection for pretreatment. One week later after the pre-treatment, $10^6$ of Sarcoma 180 cells treated or not treated with said substance are inoculated subcutaneously on the back to sensitize mouse. Further, one week after sensitization, $10^6$ of Sarcoma 180 cells are inoculated intraperitoneally and observation is continued. Proliferation of ascites cells inoculated is found to be potently inhibited only to observe less than 10% of ascites cancer cells as compared with Control group (no pre-treatment, no sensitization).

As apparently seen from the above experiments, the high molecular weight substance of the present invention seems to exhibit not only the direct effect on cancer cells but also an antitumor effect by transplantation immunity or host-mediated cancer immunity by increasing the non-specific immunity of host. This fact is further supported by the examination result according to measurement of percentage of humoral immunity producing cells, in which increase and reduction in number of plaque forming cells (PFC) appearing in spleen cells of mouse sensitized with sheep red blood cells (SRBC) are measured. Namely, when the substance obtained by the present invention is administered subcutaneously at a dose of 2.5 mg/kg per day for 4 days continuously, PFC number is increased three times as much as that of Control group, thereby exhibiting immunostimulating activity.

Most of currently available antitumor substances belong to cytotoxins and may cause anorexia, reduction in phagocyte, reduction in body weight, anaemia of liver, involution of spleen or other harmful effects. Occasionally, therefore, administration must but be discontinued. In contrast, the high molecular weight substance obtained by the present invention is free from such harmful effects. This substance rather shows potent activity for increasing non-specific immunity and suitable for administration to cancer-bearing patients with lowered immunity. Further, when therapeutical factor is examined by comparing effective concentration with toxicity, it is as much as 100 times by injection and more than 100 times by oral administration, showing extremely high safety of the present substance. Further, there is no danger of microbial cells detected on Peyer's patches of host, because no microbial cell is administered as different from the case of bacterial substances such as BCG bacteria or Streptococcus bacteria. The present substance exhibits potent effect in a very low dosage in the order of several milligrams/kg, even by oral administration, for treatment of a solid cancer for which chemical treatment has hitherto been difficult. In this respect, it can be rated as an epoch-making medicine for treatment of cancer.

The present invention is explained in further detail with reference to the following Examples.

EXAMPLE 1

To each of 24 Sakaguchi's flasks of 2 liter capacity was introduced 0.5 liter of a medium (pH 7.0) comprising 1.0% glucose, 1.0% peptone, 1.0% meat extract and 0.5% sodium chloride. The medium was autoclaved at 120° C. for 15 minutes. After each medium was cooled, 40 ml of pre-incubated culture broth in which *Acinetobacter calcoaceticus var. microformis* SC-1714 (ATCC-31299: FERM-P-4064) had been previously cultured in a medium having the same composition, was inoculated to each Sakaguchi's flask under aseptical conditions. Shaking cultivation was carried out on a shaker at 30° C. for 20 hours. After cultivation, pH of the resultant culture broth was acidic and 1 M sodium hydroxide solution was added suitably to adjust pH neutral or slightly alkaline, i.e. from 7.0 to 7.5. Under cooling at 5° C., the culture broth was subjected to centrifugation at 10,000 r.p.m. to remove microbial cells to obtain supernatant in amounts of about 11.5 liter. To 10 liter of the thus obtained culture fluid was added little by little 80 g of anhydrous calcium chloride under stirring. After all of calcium chloride was dissolved, 15 liter of acetone was added under stirring to the solution in a low temperature chamber at 5° C. and left to stand overnight in said chamber until amorphous precipitates were completely precipitated.

The resultant precipitates (I) were collected by decantation and then by suction filtration on hyflo-super cell. The precipitates (I) were dissolved again in 2 liter of water and the solution was passed through a column in which 500 ml of Dowex 1×2 (Cl type) had been packed. Then, about 500 ml of water was passed through the column in order to wash out the active substances adsorbed on the resins. The washings were combined with the previously obtained effluent and the combined liquid (2.5 liter) was subjected to lyophilization to obtain about 40 g of crude powders (II).

The crude powders (II) were dissolved in water and defatted according to the method of Folch et al. Namely, 40 g of the crude powders was dissolved in 80 ml of water and the solution was added to 3 liters of a mixed solvent comprising chloroform-methanol (volume ratio 2:1). The mixture was agitated vigorously and insolubles were collected by decantation and filtration. Said insolubles were dissolved again in 80 ml of water and the solution was added to 3 liters of a mixed solvent comprising chloroform-methanol (volume ratio 2:1). After vigorous agitation, insoluble precipitates were collected. The insoluble precipitates were dissolved again in 80 ml of water, the solution was added to 3 liters of a mixed solvent comprising chloroform-methanol (volume ratio 1:2) and the mixture was vigorously agitated. By repeating this procedure twice, white water-soluble powders were obtained. The powders were dissolved in 100 ml of water and the solution was filled in cellophane tube to perform dialysis against deionized water repeatedly, followed by lyophilization, to give about 3 g of defatted powders (III) containing SC-1714.

The defatted powders contained 16.3% of protein (Copper-Folin method, calculated as bovine serum alubumin), 30.8% of saccharide (phenol-sulfuric acid method, calculated as glucose) with elemental analysis values of C 22.3%, H 4.5%, N 4.3%, P 6.8% and Cl 0.75%. The powders showed antitumor percentage of 70% or more against mouse Sarcoma-180 solid cancer at a dosage of 5 mg/kg/one administration ×5 (intraperitoneal injection). Humoral immunity activity (measured by percentage of PFC numbers formed of SRBC-sensitized mouse) was increased by administration of said powders at a dosage of 5 mg/kg/one administration ×4 (subcutaneous injection) to more than two times as compared with Control group.

EXAMPLE 2

Two grams of the defatted powders (III) obtained in Example 1 were dissolved in a small amount of water and the solution was passed through a column in which 800 ml of carboxymethyl Sephadex (CM-Sephadex, H+type) previously activated with hydrochloric acid had been packed. The active fractions eluted with water were lyophilized to obtain powders (IV). One gram of the powders (IV) was dissolved in a suitable amount of water and the solution was passed through a column in which 500 ml of diethylaminoethyl cellulose (DEAE-cellulose, Cl− type) had been filled. After thorough washing with water, an aqueous sodium chloride solution of one mole/liter was passed to elute active substances. The fractions containing active substances were collected and filled in cellophane tube to perform dialysis against deionized water. The dialyzed solution was lyophilized to give 0.5 g of SC-1714 as white powders.

Elemental analysis: C 33.7 to 38.5%, H 4.7 to 5.7% and N 2.7 to 3.3%.

Protein content (Copper-Folin method, calculated as bovine serum alubumin) 15 to 17%.

Saccharide content (phenol-sulfuric acid method, calculated as glucose) 50 to 51%.

EXAMPLE 3

One gram of the defatted powders (III) obtained in Example 1 was dissolved in about 50 ml of water and the solution was passed through a column in which one liter of Sepharose 4 B gel had been packed. Elution with water gives the first fraction of the eluate containing potently active substances, which was collected and lyophilized to obtain 0.25 g of the objective compound as white powders.

Elemental analysis: C 38.7%, H 6.0%, N 3.5%

Protein content (Copper-Folin method, calculated as bovine serum alubumin): 13.6 to 20%

Saccharide content (phenol-sulfuric acid method, calculated as glucose): 37.5 to 40%

EXAMPLE 4

Ten liters of a medium comprising 1.0% glucose, 1.0% peptone, 0.5% meat extract and 0.5% sodium chloride were poured into 10 Erlenmeyer's flasks of 5 liter capacity equipped with buffer plates, one liter per each flask, and autoclaved at 120° C. for 15 minutes. After the medium was left to cooling, pre-incubated culture broth of *Acinetobacter calcoaceticus var. microformis* SC-1714 (ATCC 31299: FERM-P-4064), which had previously been cultured in the medium of the same composition, was inoculated aseptically, 50 ml per each Erlenmeyer's flask. Cultivation was carried out by means of a rotatory shaker at 30° C. for 24 hours. After cultivation was over, pH of the culture broth was adjusted with sodium hydroxide solution at pH 7.0 to 7.5. Under cooling at 5° C., microbial cells were removed by centrifugation. To 10 liters of the thus obtained culture fluid was added 10 g of anhydrous calcium chloride to be dissolved therein. With stirring, 15 liters of acetone was added to the solution and the mixture was left to stand overnight in an ice-room to complete precipitation. The resultant precipitates were collected by decantation and filtered by suction filtration using hyflo-super cell. The filtered precipitates were then dissolved in water and passed through a column containing Dowex 1×2 (Cl− type) resins to be decolored, whereby 2.5 liters of an aqueous solution colored in white to pale yellow was obtained. To the aqueous solution was added 4 liters of acetone to form precipitates, which were collected by decantation and filtration. The precipitates were dissolved in 200 ml of water and the solution was filled in cellophane tube to perform dialysis with deionized water. The inner dialyzed liquid was lyophilized to obtain 2.7 g of greyish white crude powders. The powders (500 mg) were dissolved in 20 ml of water and passed through a column containing 450 ml of Sepharose 4 B gel. The first fraction eluted with 0.1 M aqueous sodium chloride solution was found to have a potent activity. Said fraction was collected and dialyzed against deionized water, followed by lyophilization to give 64.5 mg of white powders (VI).

Elemental analysis: C 38.9%, H 6.9%, N 2.3%

Protein content (Copper-Folin method, calcd. as bovine serum alubumin): 7.2%

Saccharide content (Phenol-sulfuric acid method, calcd. as glucose): 25.7%

EXAMPLE 5

Using one liter of the culture fluid obtained in Example 1, ammonium sulfate powders were added thereto under stirring with cooling on an ice-water to 70% saturation concentration. Then, the resulting mixture was subjected under cooling at 5° C. to centrifugation at 10,000 r.p.m. The precipitates obtained were dissolved in a small amount of deionized water and the solution was filled in cellophane tube to perform dialysis against deionized water. After dialysis operation, the dialyzed inner solution containing the objective compound was subjected to lyophilization to obtain one gram of crude powders. The powders were defatted according to the method of Folch et al as described in Example 1. Then, according to the method as described in Example 2, eluted fractions which were not adsorbed on CM-Sephadex were adsorbed on DEAE-cellulose. The fractions eluted with 1 M aqueous sodium chloride solution were collected and dialyzed with deionized water, followed by lyophilization to obtain 80 mg of SC-1714 as white powders.

Elemental analysis: C 33.7 to 38.5%, H 4.7 to 5.7%, N 2.7 to 3.3%

Protein content (Copper-Folin method, calcd. as bovine serum alubumin): 8 to 15%

Sugar content (Phenol-sulfuric acid method, calcd. as glucose): 48 to 55%

EXAMPLE 6

The culture broth obtained in Example 1 (100 ml) was passed through Millipore filter (HAWPO 2500) and admixed with 10 mg of Streptomycin. This mixture was filled 10 injection ampoules previously sterilized of 20 ml capacity, 10 ml per each ampoule. Each ampoule was sealed by fusion with a burner and stored in a refrigerator to be ready for use by unsealing when needed.

Table 4 given below shows the antitumor activities of the substances obtained in the above Examples.

Table 4

| Example | Purification steps | Dosage | Administration method | Tumor | Solid cancer inhibitory percentage (%) | Life prolongation percentage (T/C %) |
|---|---|---|---|---|---|---|
| 1 | Precipitate(I) | 2 mg/kg × 5 | Intraperitoneal injecttion | Sarcoma 180 | 70.8 | |
| " | Precipitate(I) | " | Intraperitoneal injection | Ehrlich carcinoma | 65.0 | |
| " | Crude powder (II) | " | Intraperitoneal injection | Sarcoma 180 | 74.4 | |
| " | Crude powder (II) | " | Intraperitoneal injection | Ehrlich carcinoma | 69.0 | |
| " | Defatted powder (III) | " | Intraperitoneal injection | Sarcoma 180 | 84.0 | >180 |
| " | Defatted powder (III) | " | Intraperitoneal injection | Ehrlich carcinoma | 81.0 | >150 |
| 2 | Powder (IV) | " | Intraperitoneal injection | Sarcoma 180 | >90 | |
| " | Powder (IV) | " | Intraperitoneal injection | Ehrlich carcinoma | >90 | |

Table 4-continued

| Example | Purification steps | Dosage | Administration method | Tumor | Solid cancer inhibitory percentage (%) | Life prolongation percentage (T/C %) |
|---|---|---|---|---|---|---|
| " | White powder (SC-1714) | " | Intraperitoneal injection | Sarcoma 180 | 100 | >200 |
| " | White powder (SC-1714) | " | Intraperitoneal injection | Ehrlich carcinoma | 100 | >200 |
| 3 | White powder(V) | " | Intraperitoneal injection | Sarcoma 180 | >95 | >200 |
| " | White powder (V) | " | Intraperitoneal injection | Ehrlich carcinoma | >95 | >200 |
| 4 | White powder(VI) | " | Intraperitoneal injection | Sarcoma 180 | 100 | >200 |
| " | White powder(VI) | " | Intraperitoneal injection | Ehrlich carcinoma | >95 | >200 |
| 5 | White powder (SC-1714) | " | Intraperitoneal injection | Sarcoma 180 | 100 | >200 |
| " | White powder (SC-1714) | " | Intraperitoneal injection | Ehrlich carcinoma | 100 | >200 |
| 2&5 | White powder (SC-1714) | " | Oral administration | Sarcoma 180 | >88 | |
| " | White powder (SC-1714) | " | Intravenous injection | Sarcoma 180 | 100 | |
| " | White powder (SC-1714) | " | Subcutaneous injection | Sarcoma 180 | 95 | |
| 6 | Culture broth filtrate | 0.1 ml/mouse × 5 | Intraperitoneal injection | Sarcoma 180 | >88 | |
| " | Culture broth filtrate | 0.1 ml/mouse × 5 | Oral administration | Sarcoma 180 | 80 | |

What we claim is:

1. A substance showing antitumor activity against the ascites form of Sarcoma 18 and Ehrlich carcinoma of mouse which is prepared by culturing the microorganism; *Acinetobacter calcoaceticus var. microformis* SC-1714 (ATCC-31299; FERM-P-4064) in a suitable medium and isolating the substance having the following properties:

Physical and chemical properties

1. Appearance and solubility: obtained as white powders or films, soluble in water but insoluble in organic solvents.
2. Decomposition point: higher than 235° C.
3. Ultra-Violet absorption spectrum: as shown in FIG. 1 (for the product of Example 5), with strong absorption at around 260 nm 4. Infrared absorption spectrum (KBr tablet): as shown in FIG. 2 (for the product of Example 5), with specific absorptions at 3600, 1650, 1550 and 1100–1000 cm$^{-1}$
5. Elemental analysis: C 33.7–38.9%; H 5.2–6.9%; N 2.3–3.0%
6. Color reactions: slightly positive to ninhydrin reaction, xanthoprotein reaction and biuret reaction; positive to Molisch reaction, anthrone-sulfuric acid reaction, phenol-sulfuric acid reaction and carbazole sulfuric acid reaction.
7. Color reaction of hydrolyzed products: ninhydrin reaction intensified (after hydrolysis in 1 N HCl, at 105° C. for 24 hours); negative to phloroglucin reaction (after hydrolysis in 1 N $H_2SO_4$ at 100° C. for 4 hours)
8. Stability: Stable at pH 5 to 8 at 0° to 60° C.

Biological properties

1. Biological activity: having no antimicrobial activity, having antitumor activity against ascites form of Sarcoma 180 and Ehrlich carcimona of mouse, immunostimulating activity, anti-vaccinia virus activity, anti-inflammatory activity and activity for inhibiting secretion of acid in the stomach.
2. Acute toxicity: acute toxicity for mouse (ICR type, male, 20 to 25 g) by one dosage is as follows:
   $LD_0$ 1 g or more/kg (oral administration)
   $LD_{100}$ 300 mg/kg (intraperitoneal and and intravenous injection).

2. An antitumor substance according to claim 1 wherein the microorganism is cultured in a culture medium containing a carbon source and a nitrogen source at a pH value of about 6.0 to 7.5 at a temperature of from 25° to 35° C.

3. An antitumor substance according to claims 1 having antitumor activity as well as immunostimulatory activity, which is prepared by culturing *Acinetobacter calcoaceticus var. microformis* SC-1714 (ATCC-31299: FERM-P-4064) in a culture medium containing a carbon source and a nitrogen source at a pH value of about 6.0 to 7.5 at a temperature of from 25° to 35° C., adding to the resulted culture broth a hydrophilic organic solvent, a salt or an acid to precipitate the substance having antitumor activity as well as immunostimulatory activity, collecting the precipitates and, if desired purifying them.

4. An antitumor composition containing the substance of claim 1 which is prepared by culturing *Acinetobacter calcoaceticus var. microformis* SC-1714 (ATCC-31299: FERM-P-4064) in a fluid culture medium and removing the microbial cells from the resulted culture broth.

5. A culture broth containing the substance of claim 1 which is prepared by culturing *Acinetobacter calcoaceticus var. microformis* SC-1714 (ATCC-31299: FERM-P-4064) in a fluid culture medium containing a carbon source and a nitrogen source at a pH value of about 6.0 to 7.5 at a temperature of from 25° to 35° C.

6. A process for producing the antitumor substance of claim 1 which comprises culturing a microorganism *Acinetobacter calcoaceticus* in a suitable medium, isolating the substance having antitumor activity from the resulted culture broth and, if desired, purifying it.

7. A process according to claim 6, wherein the microorganism is cultured in a culture medium containing a carbon source and a nitrogen source at a pH value of about 6.5 to 7.5 at a temperature of about 25° to 35° C. and, to the resulted culture broth, a hydrophilic organic solvent, a salt or an acid is added to precipitate the substance having antitumor activity.

8. A pharmaceutical composition comprising antitumor substance of claim 1 and a pharmaceutically acceptable carrier.

* * * * *